United States Patent [19]

Heusser et al.

[11] Patent Number: 5,380,529
[45] Date of Patent: Jan. 10, 1995

[54] PHARMACEUTICAL, VAGINAL APPLICABLE PREPARATION AND A PROCESS FOR ITS PREPARATION

[75] Inventors: Jean Heusser, Adliswil; Michel Martin, Genève, both of Switzerland

[73] Assignee: Laboratoire Lucchini S.A., Geneve, Switzerland

[21] Appl. No.: 110,758

[22] Filed: Aug. 23, 1993

Related U.S. Application Data

[63] Continuation of Ser. No. 749,105, Aug. 23, 1991, abandoned.

[30] Foreign Application Priority Data

Jul. 10, 1990 [CH] Switzerland .................. 02294/90-5

[51] Int. Cl.$^6$ ................ A61F 6/06; A61F 13/00; A61K 31/075; A61K 31/045
[52] U.S. Cl. .................... 424/430; 424/433; 514/719; 514/738; 514/931; 514/932; 514/933; 514/934; 514/953; 514/967
[58] Field of Search ............. 424/430, 433; 514/719, 514/738, 931, 93, 933, 934, 953, 967

[56] References Cited

U.S. PATENT DOCUMENTS

| | | | |
|---|---|---|---|
| 3,875,300 | 4/1975 | Homm et al. | 424/433 |
| 4,381,772 | 5/1983 | Guistini et al. | 128/132 R |
| 4,569,837 | 2/1986 | Suzuki et al. | 424/28 |
| 4,591,501 | 5/1986 | Cioca | 424/28 |
| 4,917,901 | 4/1990 | Bourbon et al. | 424/673 |

FOREIGN PATENT DOCUMENTS 1196678 7/1970 United Kingdom .

OTHER PUBLICATIONS

Shin-Etsu Chemical Industry Co., Ltd., Chemical Abstracts, "Contraceptive Film"; 98, No. 26 Jun. 1983, p. 381, Nr. 221 811 r.
Patent Abstracts of Japan, "Contraceptive Film Pharmaceutical", vol. 7, No. 114 (C-166) [1259], May 1983.
CA 114:178498d, Diao et al., 1990.

*Primary Examiner*—Raymond J. Henley, III
*Assistant Examiner*—Kimberly R. Jordan
*Attorney, Agent, or Firm*—Burns, Doane, Swecker & Mathis

[57] ABSTRACT

The pharmaceutical, vaginal applicable preparation is characterized in that it contains, homogeneously subdivided, at least one in water soluble poly-vinyl alcohol, at least one component A, selected from the group consisting of wetting agents, non-ionic surface active agents and dispersing agents, as well as at least one active component B for the local treatment of sexually transmissible or transmitted, respectively, diseases, and/or for vaginal infections, and occasionally one or more auxiliary agent(s), and in that it is in the form of a film having a thickness of the layer of from 0.05 to 0.5 mm, especially from 0.06 to 0.2 mm, preferably from 0.07 to 0.15 mm.

21 Claims, No Drawings

PHARMACEUTICAL, VAGINAL APPLICABLE PREPARATION AND A PROCESS FOR ITS PREPARATION

This application is a continuation of application Ser. No. 07/749,105, filed Aug. 23, 1991, now abandoned.

FIELD OF THE INVENTION

The present invention is directed to a pharmaceutical, vaginal applicable preparation and to a process for its preparation.

BACKGROUND OF THE INVENTION

For the pharmaceutical treatment of vaginal diseases usually there are used vaginal tablets, ointments, gels, foams and ovuli. Each of these administrative forms has advantages and disadvantages. The disadvantages include: bad decomposition of the preparation, foreign body feeling, bad distribution of the respective active component in the vaginal mucosa, complicated dosage, for example by means of an applicator. A foam may cause an unpleasant feeling and may be rejected due to objective and/or subjective reasons. Furthermore, there is known a so-called C-film for the prevention of pregnancy.

SUMMARY OF THE INVENTION

It is an object of the present invention to provide a new galenic form, i.e. a film, for the proportioned release of the active components for the local treatment of sexually transmissible or transmitted, respectively, diseases, and/or for vaginal affections. This new galenic form shall distribute the active components on the vaginal mucosa relatively quickly, effectively and uniformly. In addition, the stability of the active compounds, which are present in the film, can be increased.

The above objects are obtained in an excellent way with the inventive preparation.

It is also an object of the present invention to provide a process for preparing the inventive preparation.

The inventive pharmaceutical, vaginal applicable preparation is characterized in that it contains, homogeneously sub-divided, at least one in water soluble polyvinyl alcohol, at least one component A, selected from the group consisting of wetting agents, non-ionic surface active agents and dispersing agents, as well as at least one active component B for the local treatment of sexually transmissible or transmitted, respectively, diseases, and/or for vaginal infections, and optionally one or more auxiliary agent(s), and in that it is in the form of a film having a thickness of from 0.05 to 0.5 mm, especially from 0.06 to 0.2 preferably from 0.07 to 0.15 mm.

The inventive process of the invention is characterized in that at least one in water soluble polyvinyl alcohol, at least one component A, selected from the group consisting of wetting agents, non-ionic surface active agents and dispersing agents, as well as at least one active component B for the local treatment of sexually transmissible or transmitted, respectively, diseases, and/or for vaginal infections, and occasionally one or more auxiliary agent(s), are mixed with water, and occasionally with at least one organic solvent, and are homogeneously sub-divided under heating, for example to a temperature of about 90° C., the so obtained mixture is poured and the solvents are removed.

DETAILED DESCRIPTION OF THE PREFERRED EMBODIMENTS

In the following part possible embodiments for preparing the inventive preparation (film) are described.

A water soluble Dolyvinyl alcohol, for example Poval 205 of Kuraray Co. Ltd., Japan, is mixed with at least one component A, for example a mixture of at least one nonoxynol, such as nonoxynols of the formula:

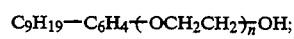

$$C_9H_{19}-C_6H_4+OCH_2CH_2\overline{)_n}OH;$$

wherein n is an integer, preferably 9 or 10, and glycerin, and with water. This mixture is then heated, for example to a temperature of about 90° C. It is preferred to filter the cooled solution, for example at a temperature of about 50° C. If the active component B and the optional auxiliary agents are soluble in water, then they can be dissolved in water and added to the mixture, preferably before filtration. If the active component B and the optional auxiliary agents are not soluble in water, then they can be added to the mixture after filtration, preferably under stirring, for example in the form of a suspension or an emulsion, whereby aqueous suspensions or aqueous emulsions are preferred. Water-in-oil microemulsions and oil-in-water microemulsions are also applicable. It is also possible to add a water insoluble active component B and/or auxiliary agent to the filtered mixture in solid form, preferably under stirring, especially when the suspension becomes homogenized. It is also possible to add the active component B and/or auxiliary agent, dissolved in at least one organic solvent, to the mixture.

In this kind of addition no separation of the phases between the organic solvent and water shall occur. If necessary for corrosion protection of film preparation devices, the filmcasting solution may be buffered.

The filtration is carried out in order to remove impurities, which may occasionally be present, such as water insoluble polymers of polyvinyl alcohol, dust and other foreign substances. In the case of absolutely pure and uniform products, the filtration can be omitted. The filmcasting solution must be homogeneous. Occasionally, any air bubbles present can be removed by leaving the solution to rest or by treating under vacuum or by performing a gentle agitation.

The filmcasting solution can now be processed by many techniques, in a conventional way, in order to obtain a film.

According to a first method, the filmcasting solution can be batch poured into a tub which has the dimensions desired. Then, the water and any occasionally present organic solvents are removed by drying. The drying can be carried out, for instance, by means of hot air, coming from a suitable hair-dryer, or coming from a suitable thermic lamp, for example an infra-red lamp. The temperature used must be such that no component is chemically transformed, especially decomposed, by the influence of heat.

The film can now be subjected to an embossing, thus increasing its surface and gripping capacity. The film is finally cut and ancillary processed, for instance packed into bags, and if necessary made sterile by a suitable irratiation method.

According to a second method, the filmcasting solution can be processed continuously in a filmcasting device. Thereby the filmcasting solution is poured onto a continuous tape through a slot nozzle. The film support is usually a strip of chrome steel polished to obtain high brightness. When pouring, the viscosity of the filmcasting solution must be such as to flow still, but not to stop.

The viscosity used depends among other things on the type of machine. The continuous tape, coated with the filmcasting solution, enters a drying tunnel, where the water and the organic solvent, which is occasionally present, are removed. The temperature in the drying tunnel must be such that no component is chemically transformed, especially decomposed, by the influence of heat. At the end of the drying tunnel, the film contains only a few percent by weight of water, for example about 5% by weight of water. The desired film thickness can be controlled and regulated by using a computer. If, when starting, the film is too thin, then the slot nozzle is automatically opened slightly. On the contrary, if the film is too thick, then the slot nozzle is closed a little bit.

With regard to the embossing, cutting and type of packaging, reference is made to the above corresponding statements.

The component B for the local treatment of sexually transmissible or transmitted, respectively, diseases, and-/or for vaginal infections is especially an active component for the local treatment of bacterial or viral infections, or an active component for the local treatment of diseases caused by a fungus or trichomonas.

Examples include: benzalkoniumchloride, neomycins, such as neomycin-B-sulfite, polymyxins, such as polymyxin-B-sulfate, econazol, econazolnitrate, metronidazol, miconazol and miconazolnitrate.

These and still other active compounds, including placenta extract, may be mixed with a non-oxynol, for example a nonoxynol of the formula:

$C_9H_{19}-C_6H_4+OCH_2CH_2)_{\overline{n}}OH$;

wherein n is an integer, preferably 9 or 10. Nonoxynol-9 and nonoxynol-10 are preferred, especially then when these compounds fulfill the prescriptions according to U.S. Pat. No. 22.

The inventive preparation is very easy to apply. It can, when cut to the desired dimensions, for example 5×5 cm, be introduced into the vagina by a finger. A foreign body feeling, if any, is only felt in the first minutes. By the influence of body heat and/or due to secretions, which are present in the vagina, the active component(s) contained in the film exhibit better and more homogenous actions, in comparison with other, particularly all solid galenic forms. The pharmaceutical effect to be obtained depends on the used combination of active components which is used.

The following examples shall illustrate the present invention.

EXAMPLE 1

Vaginal Preparation for Bacterial Infections

A mixture of 4.53 kg of polyvinyl alcohol Poval 205 of the firm Kuraray Co, Ltd., Japan, 360 g of glycerin, 2.16 kg of nonoxynol-9 and 600 g of benzalkoniumchloride was slowly warmed to a temperature of 90° C. in 17.35 kg of water under stirring. When all components had dissolved the slightly cloudy solution was cooled and filtered at a temperature of 50° C. The clear filtrate was allowed to stand at a temperature of 45° C. for 30 minutes, whereupon in the mixture no air bubbles were present in the mixture. The filmcasting solution was prepared on a filmcasting machine into a homogeneous film with a thickness of 0.09 mm. The filmcasting solution was poured at a temperature of 40° C. to 50° C.

EXAMPLE 2

Vaginal Preparation for Trichomonas

A mixture of 453 mg of polyvinyl alcohol Poval 205 of the firm Kuraray Co, Ltd., Japan, 36 mg of glycerin, 216 mg of nonoxynol-9 and 100 mg of metronidazol was dissolved in 10 ml of water and heated to a temperature of 90° C. under stirring. The slightly cloudy solution was cooled and filtered at a temperature of 50° C. This filtrate was poured into a rectangular tub (5×10 cm) and dried with a heat lamp (Biccatherm-lamp). There was obtained a homogeneous film having a thickness of 0.075 mm.

EXAMPLE 3

Vaginal Preparation for the Control of Fungus

A mixture of 3.01 kg of polyvinyl alcohol Poval 205 of the firm Kuraray Co, Ltd., Japan, 240 g of glycerin and 1.0 kg of nonoxynol was slowly warmed to a temperature of 90° C under stirring in 13.35 kg of water. The slightly cloudy solution was cooled and filtered at a temperature of 50° C. To this clear filtrate was added under stirring a slurry of 400 g of finally ground econazol in 2.0 kg of water at a temperature of 35° C. This mixture was slightly stirred at a temperature of 35° C. during 30 minutes, whereupon no more air bubbles were present in the mixture. With this filmcasting solution there was prepared a homogeneous film with a thickness of 0.07 mm on a filmcasting machine. The filmcasting solution was poured at a temperature of 35° C.

EXAMPLE 4

According to the teachings of Example 2 but without filtration, a homogeneous film (8×8 cm) was prepared with the following components:

| | |
|---|---|
| Polyvinyl alcohol Poval 205 | 435 mg |
| Glycerin | 35 mg |
| Brij 35 (a product of the firm ICI) | 300 mg |
| Econazolnitrate | 150 mg |
| | 920 mg |

At no place was this film was thicker than 0.120 mm.

EXAMPLE 5

According to the teachings of Example 2 but without filtration, a homogeneous film (5.3×6 cm) was prepared with the following components:

| | |
|---|---|
| Polyvinyl alcohol Poval 205 | 255 mg |
| Glycerin | 20 mg |
| Brij 35 (a product of the firm ICI) | 50 mg |
| Metronidazol | 100 mg |
| | 425 mg |

At no place was this film thicker than 0.120 min.

While there are shown and described present preferred embodiments of the invention, it is to be distinctly understood that the invention is not limited thereto, but may be otherwise variously embodied and practiced within the scope of the following claims.

We claim:

1. A casted and homogeneous film of a pharmaceutical, vaginally applicable preparation, effective for the proportioned release of active components of the vaginally applicable preparation, said film containing not more than about 5% by weight water and comprising, homogeneously sub-divided, (i) at least one water soluble polyvinyl alcohol, (ii) at least one component A, the component A(s) selected from the group consisting of wetting agents, non-ionic surface active agents and dispersing agents, (iii) at least one active component B, the active component B(s) selected from those compounds effective for local treatment of sexually transmissible or sexually transmitted diseases and/or vaginal infections, and, optionally, (iv) one or more auxiliary agent, wherein said film has a thickness of from about 0.05 to 0.5 mm.

2. A film of a pharmaceutical, vaginally applicable preparation according to claim 1, wherein said film has a thickness of from about 0.06 to 0.2 mm.

3. A film of a pharmaceutical, vaginally applicable preparation according to claim 2, wherein said film has a thickness of from about 0.07 to 0.15 mm.

4. A film of a pharmaceutical, vaginally applicable preparation according to claim 1, wherein at least one component B is an active component for the local treatment of bacterial or vital infections, an active component for the local treatment of a disease caused by a fungus or trichomonas, or an active component for the treatment of vaginal mucosa infections.

5. A film of a pharmaceutical, vaginally applicable preparation according to claim 4, wherein component B is selected from at least one member selected from the group consisting of benzalkoniumchloride, neomycins, polymyxins, econazol, econazolnitrate, metronidazol, miconazol, miconazolnitrate, and placenta extract.

6. A film of a pharmaceutical, vaginally applicable preparation according to claim 5, wherein component B is selected from at least one of polymyxin-B-sulfate and neomycin-B-sulfate.

7. A film of a pharmaceutical, vaginally applicable preparation according to claim 4, wherein at least one component B is mixed with at least one nonoxynol.

8. A film of a pharmaceutical, vaginally applicable preparation according to claim 7, wherein said nonoxynol has a formula:

wherein n is an integer.

9. A film of a pharmaceutical, vaginally applicable preparation according to claim 1, wherein n is 9 or 10.

10. A film of a pharmaceutical, vaginally applicable preparation according to claim 1, wherein component A is selected from polyoxyethylene ethers of fatty alcohols, monovalent alcohols, polyvalent alcohols and mixtures thereof.

11. A film of a pharmaceutical, vaginally applicable preparation according to claim 10, wherein a component A is at least one member of the group of lauryl alcohol, a nonoxynol, propylene glycol, glycerin, and mixtures thereof.

12. A film of a pharmaceutical, vaginally applicable preparation according to claim 11, wherein a component A is nonoxynol-9 or nonoxynol-10.

13. A film of a pharmaceutical, vaginally applicable preparation according to claim 11, wherein a component A is a mixture of nonoxynol and glycerin.

14. A film of a pharmaceutical, vaginally applicable preparation according to claim 1, comprising about 50 to 70% of a polyvinyl alcohol, about 15 to 35% by weight of a nonoxynol, about 3 to 8% by weight glycerin, and up to 15% by weight of active component B, wherein the total amount of said components, including the amount of any optionally present auxiliary agents, is 100% by weight.

15. A film of a pharmaceutical, vaginally applicable preparation according to claim 14, comprising about 55 to 65% by weight of a polyvinyl alcohol, about 20 to 30% by weight of a nonoxynol, and about 5% by weight of glycerin.

16. A film of a pharmaceutical, vaginally applicable preparation according to claim 1, comprising an active concentration of at least one component (iv), wherein the auxiliary agent(s) are selected from the group consisting of stabilizers, plasticizers, buffers, antioxidants, perfumes and dyes.

17. A homogeneous film having a thickness of from about 0.05 to 0.5 mm, of a pharmaceutical, vaginally applicable preparation comprising not more than about 5% by weight water, film casted without heat induced chemical transformation from a homogeneously sub-divided admixture and effective for the proportioned release of active components of the vaginally applicable preparation, said homogeneously sub-divided admixture comprising (i) at least one water soluble polyvinyl alcohol, (ii) at least one component A, the component A(s) selected from the group consisting of wetting agents, non-ionic surface active agents and dispersing agents, (iii) at least one active component B, the active component B(s) selected from those compounds effective for local treatment of sexually transmissible or sexually transmitted diseases and/or vaginal infections, and, optionally, (iv) one or more auxiliary agent.

18. A process for preparing a casted and homogeneous film of a pharmaceutical, vaginal applicable preparation, which film containing not more than about 5% by weight water and being effective for the proportioned release of active components of the vaginally applicable preparation, said process comprising mixing with water components (i)–(iii) and optionally (iv) according to claim 1, and optionally with one or more organic solvent, homogeneously sub-dividing under heat, pouring the resulting mixture and removing any solvents which may be present.

19. A process according to claim 18, wherein said heating is to a temperature of about 90° C.

20. A process according to claim 18, further comprising filtering the mixture before pouring.

21. A process according to claim 18, further comprising embossing the film to an extent effective to increase its surface.

* * * * *